United States Patent [19]

Bundy

[11] 4,161,584

[45] Jul. 17, 1979

[54] CYCLOAMIDES OF NITRILOPROSTACYCLINS

[75] Inventor: Gordon L. Bundy, Portage, Mich.

[73] Assignee: The Upjohn Company, Kalamazoo, Mich.

[21] Appl. No.: 893,586

[22] Filed: Apr. 5, 1978

Related U.S. Application Data

[63] Continuation-in-part of Ser. No. 807,514, Jun. 17, 1977, Pat. No. 4,097,489.

[51] Int. Cl.² ............................................ C07D 221/16
[52] U.S. Cl. .................. 542/421; 260/244.4; 260/326.25; 260/326.27; 260/326.5 B; 542/426; 542/429; 542/430; 542/431; 544/143; 544/144; 544/127; 544/131; 544/362; 544/373; 544/364; 546/183; 546/112; 546/187; 546/189; 546/200; 546/256; 546/272; 546/194

[58] Field of Search ...................... 260/326.25, 326.27, 260/326.5 B, 293.54, 290 HL, 297.3, 295 F, 296 B, 293.61; 544/143, 144, 127, 131, 362, 373, 364; 542/426, 421, 429, 430, 431

[56] References Cited

U.S. PATENT DOCUMENTS

| | | | |
|---|---|---|---|
| 3,931,289 | 1/1976 | Bundy | 260/473 A |
| 3,983,157 | 9/1976 | Bundy | 260/473 A |
| 3,983,158 | 9/1976 | Bundy | 260/473 A |

*Primary Examiner*—Arthur P. Demers
*Attorney, Agent, or Firm*—Robert A. Armitage

[57] ABSTRACT

This invention relates to certain structural and pharmacological analogs of prostacyclin (PGI$_2$) wherein a nitrogen atom is substituted for the 6,9α-epoxy-oxygen of prostacyclin. These novel nitrogen-containing prostacyclin-type compounds are useful for the pharmacological purposes for which prostacyclin is used, e.g., as antithrombotic agents, antihypertensive agents, antiasthma agents, nasal decongestants, or regulators of fertility and procreation.

49 Claims, No Drawings

CYCLOAMIDES OF NITRILOPROSTACYCLINS

CROSS REFERENCE TO RELATED APPLICATION

This application is a continuation-in-part of Ser. No. 807,514, filed June 17, 1977, now U.S. Pat. No. 4,097,489, issued June 27, 1978.

The present invention relates to prostacyclin analogs, the essential material constituting a disclosure thereof is incorporated here by reference from Ser. No. 807,514, filed June 17, 1977, now U.S. Pat. No. 4,097,489 issued June 27, 1978.

The present invention specifically relates to the following prostacyclin analogs:

(a) 9,11-Dideoxy-11α-hydroxymethyl-9α,6-nitrilo-PGF$_1$, piperidyl amide;
(b) 9,11-Dideoxy-9α,6-nitrilo-PGF$_1$, piperidyl amide;
(c) 9-Deoxy-9α,6-nitrilomethylene-PGF$_1$, piperidyl amide;
(d) 9-Deoxy-9α,5-nitrilo-PGF$_1$, piperidyl amide,
(e) (6R)- or (6S)-9-Deoxy-6,9α-imino-PGF$_1$, piperidyl amide;
(f) (6R)-N-methyl-6,9α-imino-PGF$_1$, piperidyl amide;
(g) (6R)-N-acetyl-6,9α-imino-PGF$_1$, piperidyl amide;
(h) (6S)-N-methyl-6,9α-imino-PGF$_1$, piperidyl amide;
(i) (6S)-N-methyl-6,9α-imino-PGF$_1$, piperidyl amide;
(j) 9-Deoxy-9α,6-nitrilo-cis-13-PGF$_1$, piperidyl amide;
(k) 9-Deoxy-9α,6-nitrilo-13,14-didehydro-PGF$_1$, piperidyl amide;
(l) 9-Deoxy-9α,6-nitrilo-14-chloro-PGF$_1$, piperidyl amide;
(m) 9-Deoxy-9α,6-nitrilo-13,14-dihydro-PGF$_1$, piperidyl amide;
(n) 2,2-Difluoro-9-deoxy-9α,6-nitrilo-15-methyl-PGF$_1$, piperidyl amide;
(o) Trans-2,3-didehydro-9-deoxy-9α,6-nitrilo-PGF$_1$, piperidyl amide;
(p) 9-Deoxy-9α,6-nitrilo-17-phenyl-18,19,20-trinor-PGF$_1$, piperidyl amide;
(q) 9-Deoxy-9α,6-nitrilo-16-phenoxy-17,18,19,20-tetranor-PGF$_1$, piperidyl amide;
(r) 9-Deoxy-9α,6-nitrilo-15-methyl-PGF$_1$, piperidyl amide;
(s) 9-Deoxy-9α,6-nitrilo-16,16-difluoro-PGF$_1$, piperidyl amide;
(t) 9-Deoxy-9α,6-nitrilo-16,16-dimethyl-PGF$_1$, piperidyl amide; and
(u) 9-Deoxy-9α,6-nitrilo-PGF$_1$, piperidyl amide.

I claim:
1. A prostacyclin analog of the formula

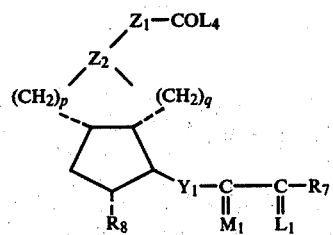

wherein R$_8$ is hydrogen, hydroxy, or hydroxymethyl
wherein Z$_2$ is

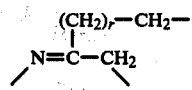

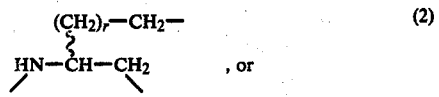

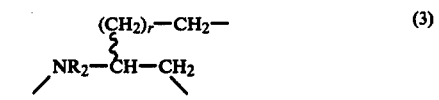

wherein R$_2$ is alkyl of one to 4 carbon atoms, inclusive, or alkylcarbonyl of one to 4 carbon atoms, inclusive;
wherein one of p, q, and r is the integer one and the other two are the integer zero;
wherein Z$_1$ is
(1) —(CH$_2$)$_g$—CH$_2$—CH$_2$—,
(2) —(CH$_2$)$_g$—CH$_2$—CF$_2$—, or
(3) trans—(CH$_2$)$_g$—CH=CH—,
wherein g is the integer zero, one, or 2;
wherein R$_4$ is hydrogen, hydroxy, or hydroxymethyl;
wherein Y$_1$ is
(1) trans—CH=CH—,
(2) cis—CH=CH—
(3) —CH$_2$CH$_2$—,
(4) trans—CH=C(Hal)—, or
(5) —C≡C—
wherein Hal is chloro or bromo;
wherein M$_1$ is

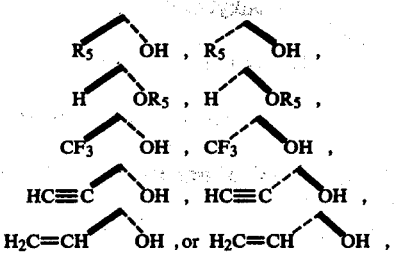

wherein R$_5$ is hydrogen or alkyl with one to 4 carbon atoms, inclusive
wherein L$_1$ is

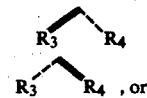

a mixture of

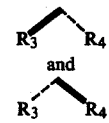

wherein R$_3$ and R$_4$ are hydrogen, methyl, or fluoro, being the same or different, with the proviso that one of R$_3$ and R$_4$ is fluoro only when the other is hydrogen or fluoro;
wherein L$_4$ is cycloamino selected from the group consisting of

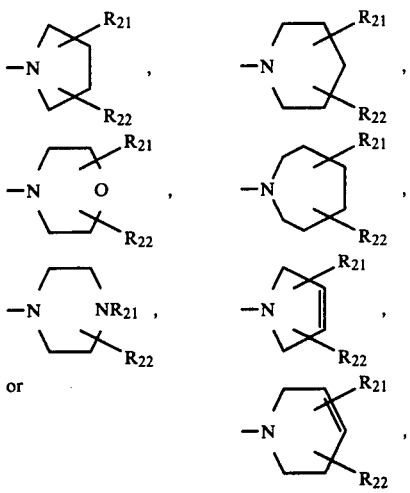

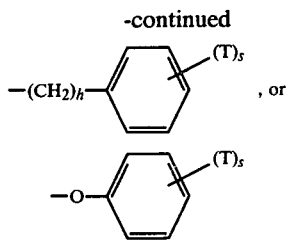

wherein $R_{21}$ and $R_{22}$ are
(i) hydrogen;
(ii) alkyl of one to 12 carbon atoms, inclusive;
(iii) cycloalkyl of 3 to 10 carbon atoms, inclusive;
(iv) aralkyl of 7 to 12 carbon atoms, inclusive;
(v) phenyl;
(vi) phenyl substituted with one, 2, or 3 chloro, alkyl of one to 3 carbon atoms, inclusive, hydroxy, carboxy, alkoxycarbonyl of one to 4 carbon atoms, inclusive, or nitro;
(vii) carboxyalkyl of one to four carbon atoms, inclusive;
(viii) carbamoylalkyl of one to four carbon atoms, inclusive;
(ix) cyanoalkyl of one to four carbon atoms, inclusive;
(x) acetylalkyl of one to four carbon atoms, inclusive;
(xi) benzoylalkyl of one to four carbon atoms, inclusive;
(xii) benzoylalkyl substituted by one, 2, or 3 chloro, alkyl of one to 3 carbon atoms, inclusive; hydroxy, alkoxy of one to 3 carbon atoms, inclusive, carboxy, alkoxycarbonyl of one to four carbon atoms, inclusive, or nitro;
(xiii) pyridyl;
(xiv) pyridyl substituted by one, 2, or 3 chloro, alkyl of one to 3 carbon atoms, inclusive; or alkoxy of one to 3 carbon atoms, inclusive;
(xv) pyridylalkyl of one to 4 carbon atoms, inclusive;
(xvi) pyridylalkyl substituted by one, 2, or 3 chloro, alkyl of one to 3 carbon atoms, inclusive, hydroxy, alkoxy of one to 3 carbon atoms;
(xvii) hydroxyalkyl of one to 4 carbon atoms, inclusive;
(xviii) dihydroxyalkyl of one to 4 carbon atoms, and
(xix) trihydroxyalkyl of one to 4 carbon atoms; with the further proviso that not more than one of $R_{21}$ and $R_{22}$ is other than hydrogen or alkyl; wherein $R_7$ is $$-(CH_2)_m-CH_3, \quad (1)$$

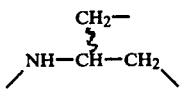

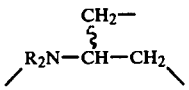

wherein m is the integer one to 5, inclusive, h is the integer zero to 3, inclusive; s is the integer zero, one, 2, or 3, and T is chloro, fluoro, trifluoromethyl, alkyl of one to 3 carbon atoms, inclusive, or alkoxy of one to 3 carbon atoms, inclusive, or with the proviso that not more than two T's are other than alkyl; and the pharmacologically acceptable acid addition salts thereof when $R_2$ is not alkylcarbonyl.

2. A prostacyclin analog according to claim 1, wherein $R_8$ is hydroxymethyl.

3. 9,11-Dideoxy-11α-hydroxymethyl-9α,6-nitrilo-PGF$_1$, piperidyl amide, a prostacyclin analog according to claim 2.

4. A prostacyclin analog according to claim 1, wherein $R_8$ is hydrogen.

5. 9,11-Dideoxy-9α,6-nitrilo-PGF$_1$, piperidyl amide, a prostacyclin analog according to claim 4.

6. A prostacyclin analog according to claim 1, wherein $R_8$ is hydroxy.

7. A prostacyclin analog according to claim 6, wherein p is one.

8. 9-Deoxy-9α,6-nitrilomethylene-PGF$_1$, piperidyl amide, a prostacyclin analog according to claim 7.

9. A prostacyclin analog according to claim 6, wherein q is one.

10. 9-Deoxy-9α,5-nitrilo-PGF$_1$, piperidyl amide, a prostacyclin analog according to claim 9.

11. A prostacyclin analog according to claim 6, wherein r is one.

12. A prostacyclin analog according to claim 11, wherein $Z_2$ is $$\begin{array}{c} CH_2- \\ NH-CH-CH_2 \end{array}$$

13. (6R)- or (6S)-9-Deoxy-6,9α-imino-PGF$_1$, piperidyl amide, a prostacyclin analog according to claim 12.

14. A prostacyclin analog according to claim 11, wherein $Z_2$ is $$\begin{array}{c} CH_2- \\ R_2N-CH-CH_2 \end{array}$$

15. (6R)-N-methyl-6,9α-imino-PGF$_1$, piperidyl amide, a prostacyclin analog according to claim 14.

16. (6R)-N-acetyl-6,9α-imino-PGF$_1$, piperidyl amide, a prostacyclin analog according to claim 14.

17. (6S)-N-methyl-6,9α-imino-PGF$_1$, piperidyl amide, a prostacyclin analog according to claim 14.

18. (6S)-N-acetyl-6,9α-imino-PGF$_1$, piperidyl amide, a prostacyclin analog according to claim 14.

19. A prostacyclin analog according to claim 11, wherein $Z_2$ is

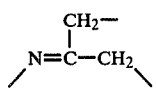

20. A prostacyclin analog according to claim 19, wherein $Y_1$ is cis—CH=CH—.
21. 9-Deoxy-9α,6-nitrilo-cis-13-PGF$_1$, piperidyl amide, a prostacyclin analog according to claim 20.
22. A prostacyclin analog according to claim 19, wherein $Y_1$ is —C≡C—.
23. 9-Deoxy-9α,6-nitrilo-13,14-didehydro-PGF$_1$, piperidyl amide, a prostacyclin analog according to claim 22.
24. A prostacyclin analog according to claim 19, wherein $Y_1$ is trans—CH=C(Hal)—.
25. 9-Deoxy-9α,6-nitrilo-14-chloro-PGF$_1$, piperidyl amide, a prostacyclin analog according to claim 24.
26. A prostacyclin analog according to claim 19, wherein $Y_1$ is —CH$_2$CH$_2$—.
27. 9-Deoxy-9α,6-nitrilo-13,14-dihydro-PGF$_1$, piperidyl amide, a prostacyclin analog according to claim 26.
28. A prostacyclin analog according to claim 19, wherein $Y_1$ is trans—CH=CH—.
29. A prostacyclin analog according to claim 28, wherein $Z_1$ is —(CH$_2$)$_g$—CH$_2$—CF$_2$.
30. 2,2-Difluoro-9-deoxy-9α,6-nitrilo-15-methyl-PGF$_1$, piperidyl amide, a prostacyclin analog according to claim 29.
31. A prostacyclin analog according to claim 28, wherein $Z_1$ is trans—(CH$_2$)$_g$—CH=CH—.
32. Trans—2,3—didehydro-9-deoxy-9α,6-nitrilo-PGF$_1$, piperidyl amide, a prostacyclin analog according to claim 31.
33. A prostacyclin analog according to claim 28, wherein $Z_1$ is —(CH$_2$)$_g$—CH$_2$—CH$_2$—.
34. A prostacyclin analog according to claim 33, wherein g is zero.
35. A prostacyclin analog according to claim 34, wherein $R_7$ is

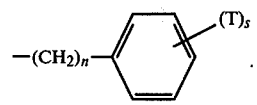

36. 9-Deoxy-9α,6-nitrilo-17-phenyl-18,19,20-trinor-PGF$_1$, piperidyl amide, a prostacyclin analog according to claim 35.
37. A prostacyclin analog according to claim 34, wherein $R_7$ is

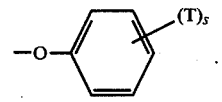

38. 9-Deoxy-9α,6-nitrilo-16-phenoxy-17,18,19,20-tetranor-PGF$_1$, piperidyl amide, a prostacyclin analog according to claim 37.
39. A prostacyclin analog according to claim 34, wherein $R_7$ is —(CH$_2$)$_m$—CH$_3$—.
40. A prostacyclin analog according to claim 39, wherein m is 3.
41. A prostacyclin analog according to claim 40, wherein $R_5$ is methyl.
42. 9-Deoxy-9α,6-nitrilo-15-methyl-PGF$_1$, piperidyl amide, a prostacyclin analog according to claim 41.
43. A prostacyclin analog according to claim 40, wherein $R_5$ is hydrogen.
44. A prostacyclin analog according to claim 43, wherein at least one of $R_3$ and $R_4$ is fluoro.
45. 9-Deoxy-9α,6-nitrilo-16,16-difluoro-PGF$_1$, piperidyl amide, a prostacyclin analog according to claim 44.
46. A prostacyclin analog according to claim 43, wherein at least one of $R_3$ and $R_4$ is methyl.
47. 9-Deoxy-9α,6-nitrilo-16,16-dimethyl-PGF$_1$, piperidyl amide, a prostacyclin analog according to claim 46.
48. A prostacyclin analog according to claim 43, wherein $R_3$ and $R_4$ are both hydrogen.
49. 9-Deoxy-9α,6-nitrilo-PGF$_1$, piperidyl amide, a prostacyclin analog according to claim 48.

* * * * *

UNITED STATES PATENT OFFICE
CERTIFICATE OF CORRECTION

Patent No. 4,161,584           Dated July 17, 1979

Inventor(s) Gordon L. Bundy

It is certified that error appears in the above-identified patent and that said Letters Patent are hereby corrected as shown below:

Column 4, lines 44-49, "
$$\begin{array}{c} CH_2- \\ \text{\Large )} \\ NH-CH-CH_2 \end{array}$$
" should read --
$$\begin{array}{c} CH_2-CH_2- \\ \text{\Large )} \\ NH-CH-CH_2 \end{array}$$
--

Column 4, lines 55-60, "
$$\begin{array}{c} CH_2- \\ \text{\Large (} \\ R_2N-CH-CH_2 \end{array}$$
" should read --
$$\begin{array}{c} CH_2-CH_2- \\ \text{\Large (} \\ R_2N-CH-CH_2 \end{array}$$
--

Column 5, lines 3-8, "
$$\begin{array}{c} CH_2- \\ | \\ N=C-CH_2 \end{array}$$
" -- 
$$\begin{array}{c} CH_2-CH_2- \\ | \\ N=C-CH_2 \end{array}$$
--

Column 6, lines 1-6, "

$$-(CH_2)_n-\bigcirc-(T)_s$$

should read $$-(CH_2)_h-\bigcirc-(T)_s$$

[SEAL]

Signed and Sealed this

Twenty-ninth Day of January 1980

Attest:

SIDNEY A. DIAMOND

*Attesting Officer*     *Commissioner of Patents and Trademarks*